US012793217B2

(12) United States Patent
Chen et al.

(10) Patent No.: US 12,793,217 B2
(45) Date of Patent: Nov. 10, 2026

(54) OPTIMAL PATH FINDING BASED SPINAL CENTER LINE EXTRACTION

(71) Applicant: KONINKLIJKE PHILIPS N.V., Eindhoven (NL)

(72) Inventors: Hongxin Chen, Shanghai (CN); Christian Buerger, Hamburg (DE); Tobias Klinder, Uelzen (DE); Cristian Lorenz, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 137 days.

(21) Appl. No.: 18/845,145

(22) PCT Filed: Mar. 7, 2023

(86) PCT No.: PCT/EP2023/055645
§ 371 (c)(1),
(2) Date: Sep. 9, 2024

(87) PCT Pub. No.: WO2023/170010
PCT Pub. Date: Sep. 14, 2023

(65) Prior Publication Data
US 2025/0200744 A1 Jun. 19, 2025

(30) Foreign Application Priority Data
Mar. 11, 2022 (WO) ................ PCT/CN2022/080342
May 4, 2022 (EP) .................................... 22171688

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/4566* (2013.01); *G06T 7/10* (2017.01);
(Continued)

(58) Field of Classification Search
CPC ......... G06T 7/0012; G06T 2207/30012; G06T 2207/30172; G06T 2207/10081; A61B 5/4566; G16H 30/20
See application file for complete search history.

(56) References Cited

U.S. PATENT DOCUMENTS 6,850,635 B2 * 2/2005 Gerard .................. G16H 30/40 382/190
7,046,830 B2 * 5/2006 Gerard ...................... G06T 7/60 382/128
(Continued)

FOREIGN PATENT DOCUMENTS

CN 101790748 A * 7/2010 ............... G06T 7/11
CN 109919903 A * 6/2019
(Continued)

OTHER PUBLICATIONS

Koh, J., Chaudhary, V., Jeon, E. K., & Dhillon, G. (2014). Automatic spinal canal detection in lumbar MR images in the sagittal view using dynamic programming. Computerized medical imaging and graphics, 38(7), 569-579. (Year: 2014).*
(Continued)

*Primary Examiner* — Michael Robert Cammarata
(74) *Attorney, Agent, or Firm* — Larry Liberchuk

(57) ABSTRACT

Method and apparatus for finding an optimal spinal canal path center line are disclosed. Imaging scans such as a Computer Tomography (CT) scan are used to diagnosis rib and spine fractures. The spine image is usually reformatted in a straightened CPR (curved planar reformat). A dynamic programming-based techniques to find an optimal path from a spinal canal segmentation is disclosed. The disclosed method and apparatus overcomes spinal canal segmentation errors resulting in spinal canal gaps and unrealistic image distortions. The disclosed techniques are not sensitive to segmentation errors even is the presence of high segmenta-
(Continued)

tion noise. The disclosed techniques generate a binary three-dimensional image corresponding to the scanned spine image, perform density estimation to create a three-dimensional having the same size as the original binary three-dimensional, perform dynamic programming based optimal spinal canal path finding with a coarse to fine optimal path finding strategy to accelerate the optimal spinal canal path finding.

13 Claims, 5 Drawing Sheets

(51) Int. Cl.

*G06T 7/10* (2017.01)
*G06T 7/66* (2017.01)
*G06T 15/00* (2011.01)
*G16H 30/20* (2018.01)
*G16H 30/40* (2018.01)

(52) U.S. Cl.

CPC ................ *G06T 7/66* (2017.01); *G06T 15/00* (2013.01); *G16H 30/20* (2018.01); *G16H 30/40* (2018.01); *G06T 2207/30012* (2013.01)

(56) References Cited

U.S. PATENT DOCUMENTS

| | | | | |
|---|---|---|---|---|
| 12,433,678 | B2 * | 10/2025 | Benson | A61B 34/10 |
| 2002/0136437 | A1 * | 9/2002 | Gerard | G06T 7/60 382/128 |
| 2014/0161331 | A1 * | 6/2014 | Cohen | G06T 5/73 382/128 |
| 2014/0254907 | A1 * | 9/2014 | Wang | G06T 7/143 382/131 |
| 2022/0245400 | A1 * | 8/2022 | Siemionow | A61B 5/4058 |

FOREIGN PATENT DOCUMENTS

| | | | | |
|---|---|---|---|---|
| CN | 111462071 A * | 7/2020 | G06N 7/01 |
| CN | 109919903 B * | 8/2020 | |
| WO | WO2017074890 A1 | 5/2017 | |

OTHER PUBLICATIONS

Beulah, A., T. Sree Sharmila, and T. Kanmani. "Spinal cord segmentation in lumbar mr images." International Conference on Emerging Current Trends in Computing and Expert Technology. Cham: Springer International Publishing, 2019. (Year: 2019).*
Liao, C.C., Ting, H.W., Xiao, F.: Atlas-free cervical spinal cord segmentation on midsagittal t2-weighted magnetic resonance images. J. Healthc. Eng. (2017) (Year: 2017).*
Q. Wang et al., "Automatic Segmentation of Spinal Canals in CT Images via Iterative Topology Refinement," in IEEE Transactions on Medical Imaging, vol. 34, No. 8, pp. 1694-1704, Aug. 2015, doi: 10.1109/TMI.2015.2436693. (Year: 2015).*
A. Díaz-Parra, E. Arana and D. Moratal, "A fully automated method for spinal canal detection in computed tomography images," 2014 36th Annual International Conference of the IEEE Engineering in Medicine and Biology Society, Chicago, IL, USA, 2014, pp. 5514-5517, doi: 10.1109/EMBC.2014.6944875. (Year: 2014).*
PCT International Search Report, International application No. PCT/EP2023/055645, Mar. 21, 2023.
Koh J. et al., "Automatic Spinal Canal Detection in Lumbar MR Images in the Sagittal View Using Dynamic Programming", Computerized Medical Imaging and Graphics, Pergamon Press, New York, NY, US, vol. 38, No. 7, Jun. 18, 2014 (Jun. 18, 2014), pp. 569-579, XP029064015.
Vrtovec T. et al., "Automated Generation of Curved Planar Reformations from MR Images of the Spine", Physics in Medicine and Biology, Institute of Physics Publishing, Bristol GB, vol. 52, No. 10, May 21, 2007 (May 21, 2007), pp. 2865-2878, XP020112878.
Rak M. et al., "On Computerized Methods for Spine Analysis in MRI: A Systematic Review", International Journal of Computer Assisted Radiology and Surgery, Springer, DE, vol. 11, No. 8, Feb. 9, 2016 (Feb. 9, 2016), pp. 1445-1465, XP036013992.

* cited by examiner

202

204

OPTIMAL PATH FINDING BASED SPINAL CENTER LINE EXTRACTION

FIELD OF THE INVENTION

The invention relates to the field of medical imaging, in particular to a method and apparatus of extracting a spinal canal center line that is not sensitive to segmentation errors.

BACKGROUND OF THE INVENTION

Medical imaging is often used to visualize a patient's anatomy where the visualization data is used to diagnose diseases or injuries. In a trauma setting, medical personnel will often perform an imaging scan such as a Computer Tomography (CT) scan to diagnose fractures of the ribs and spine.

To help a radiologist read the CT spine image, the spine image is often reformatted in a straightened curved planar reformat (CPR). The reformatted image may be a straightened view in 2D or 3D according to the spinal canal curve. The first step in generating the reformatted image is to extract the center line of the spinal canal. This is typically accomplished by executing a three-dimensional (3D) spinal canal segmentation and then extracting the center line of the segmentation. If the segmentation result is good, extracting the center line may not be difficult. Frequently, however, there are some errors in the segmentation. On occasion, part of the spinal canal is missed (gaps in between slices). On other occasions, there are false segmentations where the predicted spinal canal does not reflect that actual spinal canal. These issues create complex challenges to the center line extraction.

If the extracted spinal canal center line is incorrect, the reformatted image will also be incorrect leading to unrealistic image distortions within the resulting image. Reading imaging scans, and more specifically trauma or Emergency Department scans, is a time-critical task that needs to be done with high attention to avoid overlooking critical findings. Reformatting an image scan to a straightened view in 2D or 3D according to the spinal canal curve is performed to aid medical professionals diagnosing critical rib and spine fractures. A reformatted image with unrealistic image distortions defeats the purpose of the reformatted image.

Thus, the need exists for innovative techniques to extract a spinal canal center that are not sensitive to segmentation errors.

SUMMARY OF THE INVENTION

The object of the present invention provides techniques for extracting a spinal canal center that are not sensitive to segmentation errors. The techniques may be applied to virtually any spine image that is reformatted to a straightened view in 2D or 3D according to the spinal canal curve. These spine images may be generated by a number of imaging systems including CT, CT-arm, Single Photon Emission Computer Tomography CT (SPECT-CT), Magnetic Resonance CT (MR-CT), Positron Emission Tomography CT (PET-CT), and Magnetic Resonance Imaging (MRI) systems.

According to a first aspect of the invention a method of generating an optimal spinal canal is provided. The method comprising receiving scan data as a three-dimensional array of a scanned spine image and executing a three-dimensional voxel wise spinal canal segmentation from the received scan data to generate a binary three-dimensional array corresponding to the scanned spine image. Generating an inverse density three-dimensional array corresponding to the generated binary three-dimensional array having a size the same as the generated binary three-dimensional array, down sampling the inverse density three-dimensional array to a predetermined size, performing programming based optimal spinal canal path finding to generate an optimal spinal canal path, sampling the inverse three-dimensional array around the generated optimal spinal canal path with higher resolution and limited size, performing programming based optimal spinal canal path finding to generate a revised optimal spinal canal path, repeating the sampling and the programming based optimal spinal canal path finding by incrementally increasing the resolution and decreasing the size, determining whether an accuracy of the optimal spinal canal path satisfies a predetermined threshold, and generating a final optimal spinal canal path as a spinal canal center line, wherein a reformatted image is generated according to the final optimal spinal canal path as a spinal canal center line.

According to a second aspect of the invention an optimal path find apparatus is provided. The apparatus comprises a memory configured to store computer executable instructions and at least one processor configured to execute the computer executable instructions to cause the optimal path find apparatus to receive scan data as a three-dimensional array of a scanned spine image, execute a three-dimensional voxel wise spinal canal segmentation from the received scan data to generate a binary three-dimensional array corresponding to the scanned spine image, generate an inverse density three-dimensional array corresponding to the generated binary three-dimensional array having a size the same as the generated binary three-dimensional array, down sample the inverse density three-dimensional array to a predetermined size, perform programming based optimal spinal canal path finding to generate an optimal spinal canal path, sample the inverse three-dimensional array around the generated optimal spinal canal path with higher resolution and limited size, perform programming based optimal spinal canal path finding to generate a revised optimal spinal canal path, repeat the sampling and the programming based optimal spinal canal path finding by incrementally increasing the resolution and decreasing the size, determine whether an accuracy of the optimal spinal canal path satisfies a predetermined threshold, and generate a final optimal spinal canal path as a spinal canal center line, wherein a reformatted image is generated according to the final optimal spinal canal path as a spinal canal center line.

In a third aspect of the invention, a non-transitory computer-readable medium having stored thereon instructions for causing processing circuitry to execute a process is provided. The process comprises receiving scan data as a three-dimensional array of a scanned spine image, executing a three-dimensional voxel wise spinal canal segmentation from the received scan data to generate a binary three-dimensional array corresponding to the scanned spine image, generating an inverse density three-dimensional array corresponding to the generated binary three-dimensional array having a size the same as the generated binary three-dimensional array, down sampling the inverse density three-dimensional array to a predetermined size, performing programming based optimal spinal canal path finding to generate an optimal spinal canal path, sampling the inverse three-dimensional array around the generated optimal spinal canal path with higher resolution and limited size, performing programming based optimal spinal canal path finding to generate a revised optimal spinal canal path, repeating the sampling and the programming based optimal spinal canal path finding by incrementally increasing the resolution and decreasing the size, determining whether an accuracy of the optimal spinal canal path satisfies a predetermined threshold, and generating a final optimal spinal canal path as a spinal canal center line, wherein a reformatted image is generated according to the final optimal spinal canal path as a spinal canal center line.

In an embodiment, spinal canal segmentation is performed using machine or deep learning techniques, wherein a value of 1 is assigned to each spinal canal voxel and a value of 0 is assigned to background in the generated binary three-dimensional array. A float value is assigned to each voxel in the inverse density three-dimensional array, where the higher a density value of 1 voxels are in the binary three-dimensional array, the lower the float value is assigned to a corresponding voxel in the inverse density three-dimensional array.

In another embodiment, a cost-pointer array is created, the cost-pointer array corresponding to the inverse density three-dimensional array, wherein each element in the cost-pointer array comprises a cost component and a pointer component, wherein each cost component in the cost-pointer array corresponds to a voxel in a same position in the inverse density three-dimensional array, and wherein the pointer component is a three-dimensional vector which points to a physical coordinate in the binary three-dimensional array.

In a preferred embodiment, the programming based optimal spinal canal path finding is dynamic programming based optimal spinal canal path finding. A density estimation is applied to generate the inverse density three-dimensional array, where the density estimation is performed via kernel density estimation techniques, and wherein the kernel is at least one of gaussian, linear, cosine, uniform, epanechnikov, exponential, and tophat.

DETAILED DESCRIPTION OF EMBODIMENTS

Figure 1:
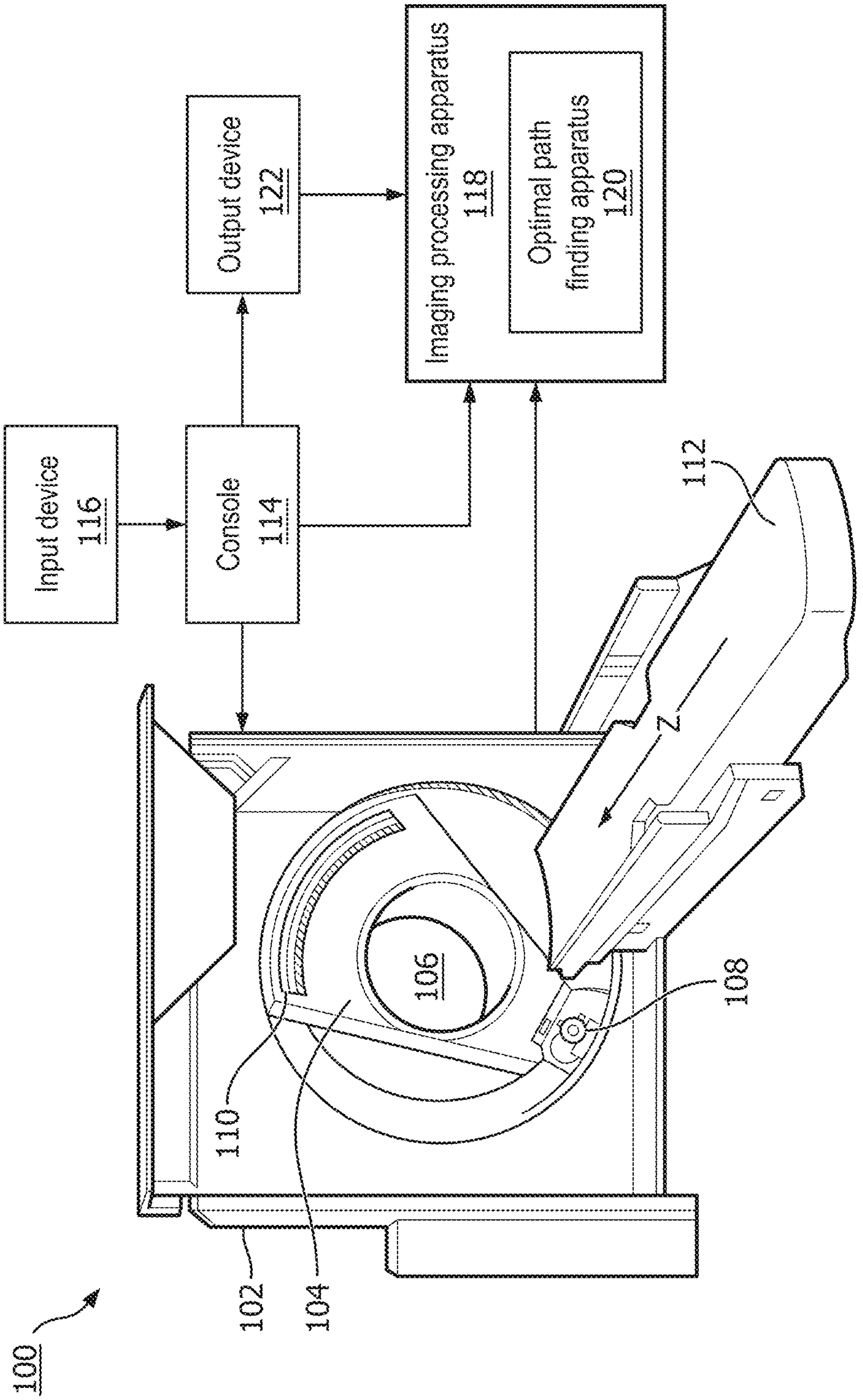
FIG. 1 is a diagram of an exemplary imaging system.

FIG. 1 illustrates an imaging system 100 such as a computed tomography (CT) imaging system. The imaging system 100 includes a generally stationary gantry 102 and a rotating gantry 104. The rotating gantry 104 is rotatably supported by the stationary gantry 102 and rotates in relation to the stationary gantry 102 around an examination region 106 about a longitudinal or z-axis.

A patient support 112, such as a couch, supports an object or examination subject such as a human patient in the examination region 106. The support 112 is configured to move the object or examination subject for loading, scanning, and unloading of the object or examination subject.

A radiation source 108, such as an x-ray tube, is rotatably supported by the rotating gantry 104. The radiation source 108 rotates with the rotating gantry 104 and emits radiation that traverses the examination region 106.

A radiation sensitive detector array 110 subtends an angular arc opposite the radiation source 108 across the examination region 106. The detector array 110 includes one or more rows of detectors that extend along the z-axis direction, detects radiation traversing the examination region 106, and generates projection data indicative thereof.

A general-purpose computing system or computer serves as an operator console 114 and includes an input device(s) 116 such as a mouse, a keyboard, and/or the like and an output device(s) 122 such as a display monitor, a filmer or the like. The console 114 allows an operator to control the operation of the system 100. This includes control of an imaging processing apparatus 118. The imaging processing apparatus includes optimal path finding apparatus 120. The imaging processing apparatus 118 receives data representative of a three-dimensional (3D) diagnostic image generated by the imaging system 100 and generates a reformatted image displaying a continuous and straightened visualization of a rib cage and spine. The reformatted image may be output to output device 122 for reading by medical personal.

Optimal path finding apparatus 120 may be configured as part of imaging processing apparatus 118 or configured external to imaging processing apparatus 118. It is to be appreciated that optimal path finding apparatus 120 can be implemented through a microprocessor(s), which executes a computer readable instruction(s) encoded or embedded on computer readable storage medium such as physical memory and other non-transitory medium. Additionally or alternatively, the microprocessor(s) can execute a computer readable instruction(s) carried by a carrier wave, a signal and other transitory (or non, non-transitory) medium.

The optimal path finding apparatus 120 receives scan data as a 3D array of a scanned spine image. The 3D array of a scanned spine image may be generated by imaging processing apparatus 118 of imaging system 100. Optimal path finding apparatus 120 performs spinal canal segmentation by executing a three-dimensional voxel wise spinal canal segmentation from the received scan data to generate a binary three-dimensional array corresponding to the scanned spine image. Optimal path finding apparatus 120 generates an inverse density 3D array corresponding to the generated binary 3D array, the inverse density 3D array having a size the same as the generated binary three-dimensional array. The rationale for generating the inverse density 3D array will be explained in more detail later. Optimal path finding apparatus 120 performs down sampling of the inverse density 3D array to a predetermined size and programming based optimal spinal canal path finding to generate an optimal spinal canal path.

The programming based optimal spinal canal path finding is then performed to generate a revised optimal spinal canal path. The sampling and the programming based optimal spinal canal path finding is repeated until the accuracy of the optimal spinal path satisfies a predetermined threshold. The sampling is repeated around the 3D density image volume with higher resolution and limited size each time. The programming based optimal spinal canal path finding is repeated for each repeated sampling with a higher resolution and limited size, and the accuracy of the generated optimal path increases with each sampling cycle. This is an example of a coarse to fine strategy that is implemented to accelerate the optimal path finding. Once the optimal spinal path satisfies the predetermined threshold, a final optimal spinal canal path is generated as a spinal canal center line. A reformatted image can then be generated with the final optimal spinal canal path as a spinal canal center line.

Figure 2:
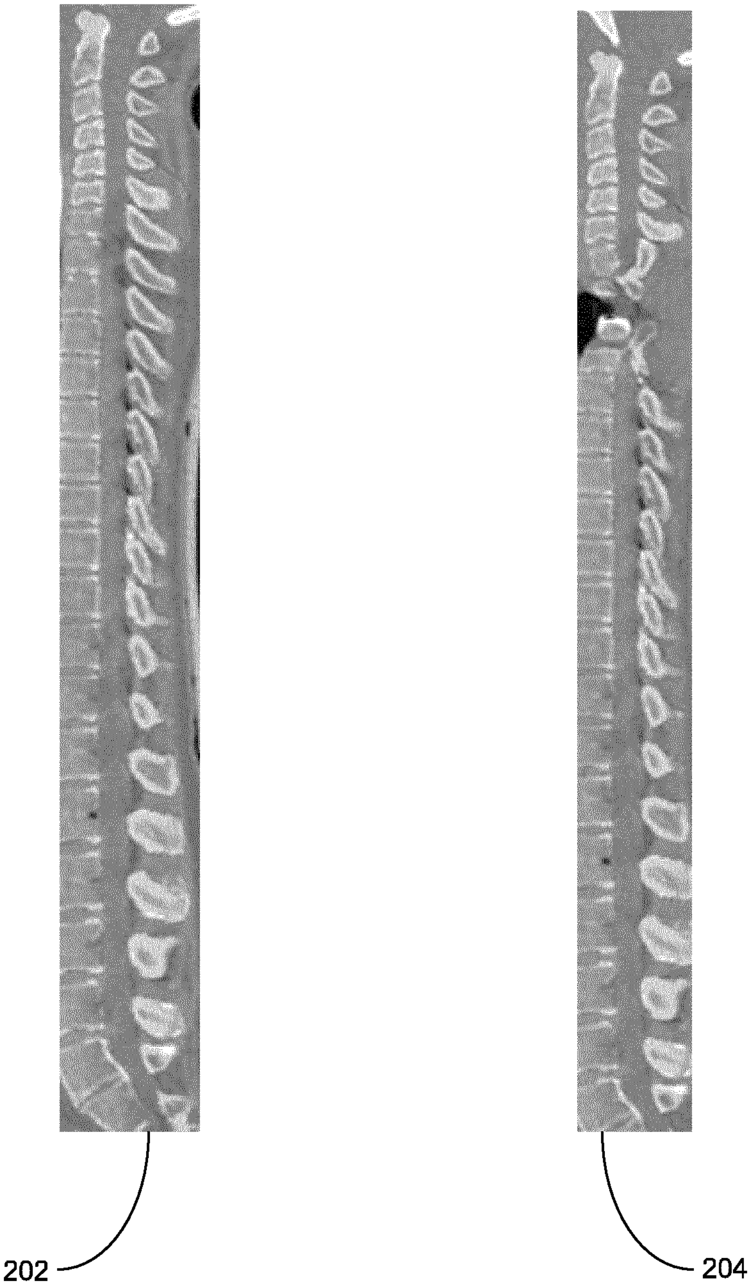
FIG. 2 illustrates an example of a straightened CPR without errors in the spine segmentation and center line extraction and a straightened spine with errors in the spine segmentation and center line extraction.

FIG. 2 is an example of a straightened CPR without errors in the spine segmentation and center line extraction and a straightened spine with errors in the spine segmentation and center line extraction. A reformatted image with a correctly extracted spinal canal center line is shown at 202. A reformatted image with errors in the extracted spinal canal center line is shown at 204. The reformatted image at 204 illustrates a reformatted image with unrealistic image distortions and a gap between slices. Thus, the reformatted image at 204 would not aid medical personnel performing a diagnosis.

Figure 3:
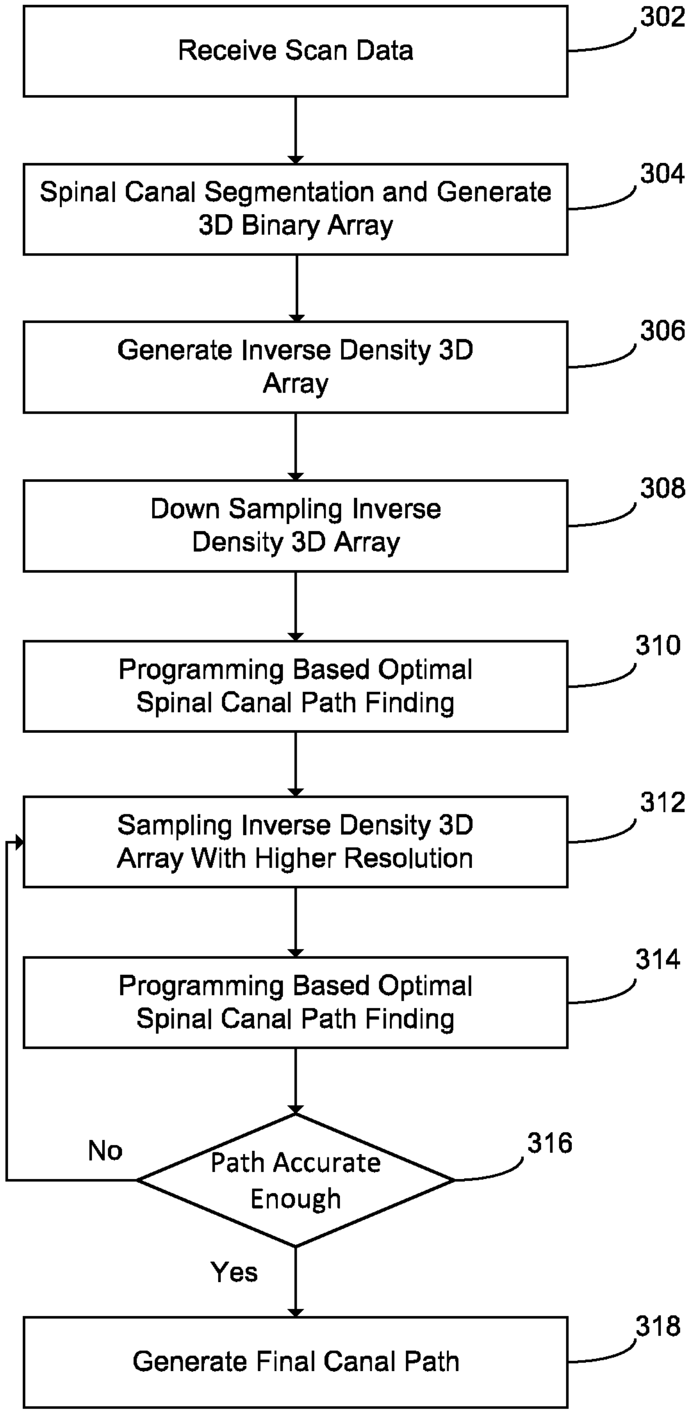
FIG. 3 is a flowchart representing a method generating a combined rib and spine view according to some embodiments.

FIG. 3 is a flowchart representing a method generating a combined rib and spine view according to one embodiment. Image scan data is received at 302. The image scan data is a 3D array where each element in the 3D array represents a voxel. At 304, a 3D voxel wise spinal canal segmentation is performed using the received scan data to generate a binary 3D array corresponding to the scanned spine image. In the generated 3D binary array, a value "1" indicates a spinal canal voxel and a value "0" indicates background. The spinal canal segmentation may be performed by any deep learning or machine learning method or some other conventional algorithm.

At 306, an inverse density 3D array is generated. In the generated 3D binary array, the value "1" indicates a spinal canal voxel and the value "0" indicates background. After generating the inverse density 3D array, the higher the density of the "1" voxels in the original volume are, the lower the value will be assigned to the voxel in the inverse density volume.

If the optimal path finding is performed over the whole inverse density volume with full resolution, the process is likely to be very demanding on the available resources and the process will likely be slow. Therefore, in an embodiment, a course to fine optimal path finding strategy is implemented to accelerate the process. At 308, down sampling of the inverse density 3D array to a predetermined size is performed. In other words, the inverse density 3D array is down sampled to a low-resolution array Programming based optimal spinal canal path finding to generate an optimal spinal canal path is performed at 310. Then at 312, the inverse density 3D array is sampled around the image volume of the optimal spinal canal path generated at 310. The sampling at 312 is performed with a limited size and higher resolution.

At 314, the programming based optimal spinal canal path finding is performed on the sampled image volume 312 to generate a revised optimal spinal canal path. The sampling at 312 and programming based optimal spinal canal path finding at 314 are repeated until the accuracy of the optimal spinal canal satisfies a predetermined threshold. When the accuracy of the optimal spinal canal satisfies the predetermined threshold at 316, a final optimal spinal canal path is generated at 318. A reformatted image may then be generated with the final optimal spinal canal path generated at 318.

Figure 4:
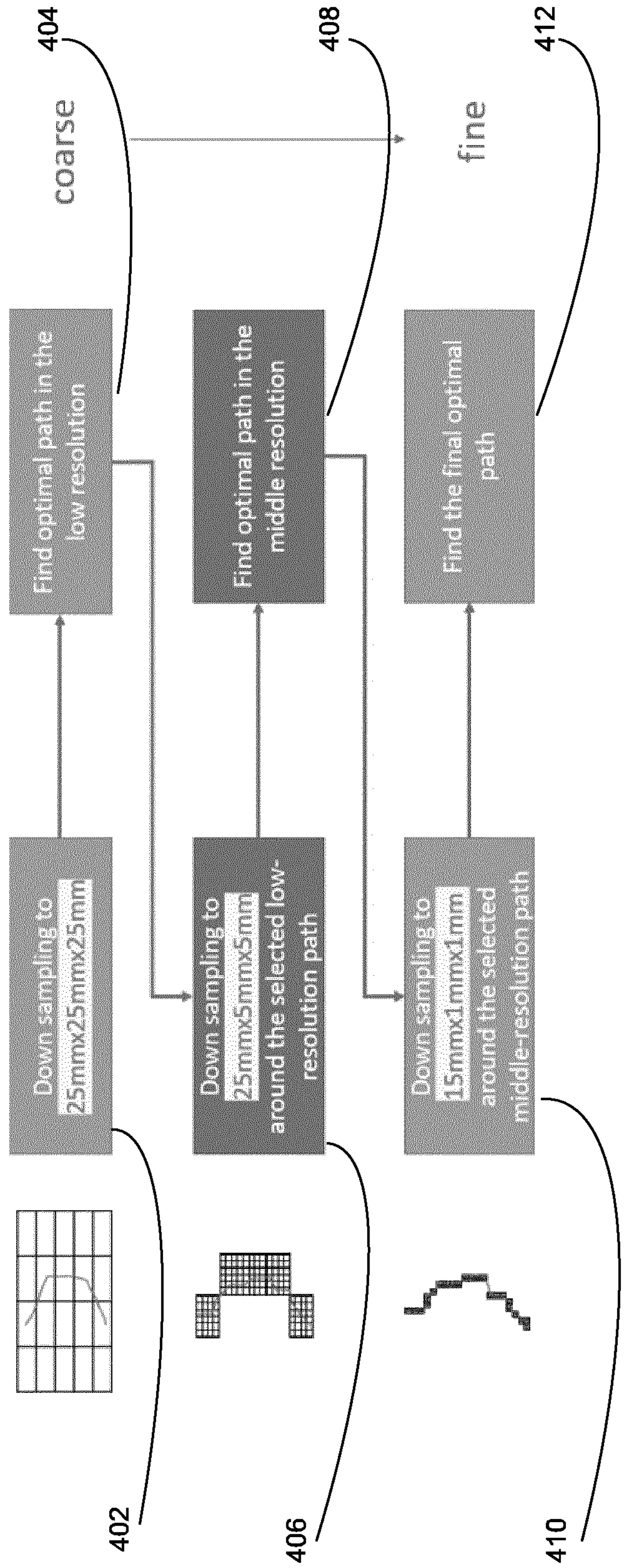
FIG. 4 illustrates an example of a coarse to fine optimal path finding approach according to some embodiments.

FIG. 4 illustrates an example of the coarse to fine optimal path finding approach according to an embodiment.

At 402, the inverse density 3D array is down sampled to a predetermined resolution. As illustrated in 402, the predetermined resolution is 25 mm×25 mm×25 mm. That is, the sampling is performed once every 25 mm along the z axes, every 25 mm around the x axes, and every 25 mm around the y axes. The resolution illustrated in 402, 406, and 410 is used for ease of illustration and should not be construed as limiting the scope.

At 404, programming based optimal spinal canal path finding is performed to generate a low resolution optimal spinal canal path. At 406, the inverse density 3D array is down sampled in a limited size of volume around the optimal spinal canal path generated at 404 with resolution 25 mm×5 mm×5 mm. Here, the sampling is performed once every 25 mm along the z axes, every 5 mm around the x axes, and every 5 mm around the y axes. Thus, the resolution is increased.

Programming based optimal spinal canal path finding is performed at 408 to generate a revised optimal spinal canal path with higher resolution (middle resolution). Down sampling is performed at 410 in a limited size of volume around the optimal spinal canal path generated at 408 with resolution 15 mm×1 mm×1 mm. Here, the sampling is performed once every 15 mm along the z axes, every 1 mm around the x axes, and every 1 mm around the y axes. Thus, the resolution is further increased. Programming based optimal spinal canal path finding is performed at 412 to generate a final optimal spinal canal path with high resolution.

While the coarse to fine strategy illustrated in FIG. 4 comprises three cycles of down sampling and optimal path finding, it should be understood that this is for ease of description and not be construed as limiting the scope.

Figure 5:
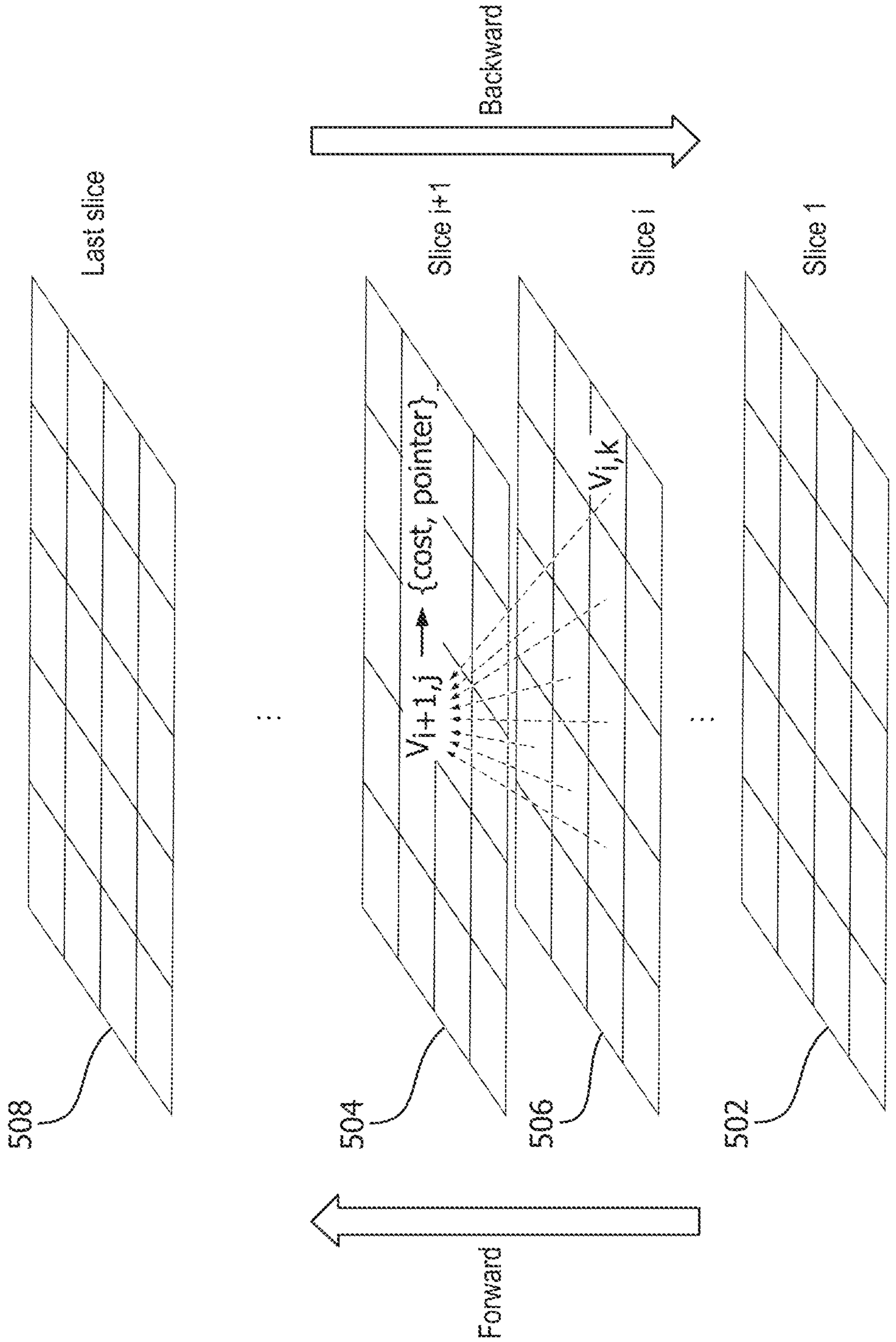
FIG. 5 illustrates three-dimensional optimal path finding according to some embodiments.

FIG. 5 illustrates three-dimensional optimal path finding according to a cost analysis.

Typically, the spinal canal is monotonically moving up from the sacrum to the head. After segmentation, in the predicted spinal canal binary 3D array, if a high cost is assigned to the background voxels and low cost is assigned to the predicted spinal canal voxels, then even in the presence of noise, as long as the actual spinal canal voxels dominate the foreground, a path from a bottom slice to a top slice with lowest cost will be along the actual spinal canal. Furthermore, for the predicted spinal canal voxels, if we assign a low cost to voxels with high density and a high cost to voxels with low density, the shortest path with lowest cost will be along the center line of the actual spinal canal since the spinal canal center usually has a higher density.

Finding the optimal path from sacrum to head or from head to sacrum can use a dynamic programming method. Starting from the second slice of the 3D binary array, each voxel will calculate costs from neighboring voxels in the last slice to it. The neighboring voxels can cover a small area or all the voxels in the last slice. The cost contains three parts. The first part is the physical distance from a voxel in last slice to the current voxel in the current slice. The second part is the inverse of density of the selected voxel in last slice. The reason to use inverse density is to find an optimal path with lowest accumulated cost, but the path needs to pass voxels with as a high density as possible. Thus, the inverse of density will make high density contribute less to the accumulated cost.

The density estimation can use a kernel density estimation method. The kernel could be gaussian, linear, cosine, etc. Using a kernel density can reduce the impact of the contribution of outliers to the density of a given voxel. Given a voxel, the estimated density will consider the number of voxels around it. The density can be 3D density or the slice level 2D density.

The third part is the cost already calculated in the last slice for the selected voxel. For each voxel in the current slice, after calculating the costs from the neighboring voxels in the last slice to it, a pointer is assigned to the current voxel pointing to the neighboring voxel in the last slice with lowest cost, and this lowest cost is set as the accumulated cost for the current voxel. After performing calculations from the first slice to the last slice, each voxel in the last slice has a cost value and a pointer value pointing to a voxel in the second last slice. Then starting from the last slice find the optimal path as follows. In the last slice, find the voxel with lowest cost. This is the start voxel. According to the pointer assigned to that voxel, find a second voxel in the second to last slice. Then according to the pointer assigned to the second voxel, we can find a third voxel in the third to last slice. So, slice by slice, an optimal path by linking all the pointers together can be generated.

As indicated with reference to FIG. 3, a 3D voxel wise spinal canal segmentation is performed using the received scan data to generate a binary 3D array corresponding to the scanned spine image. In the generated 3D binary array, a value "1" indicates a spinal canal voxel and a value "0" indicates background. An inverse density 3D array is generated. In the generated 3D binary array, the value "1" indicates a spinal canal voxel and the value "0" indicates background. After generating the inverse density 3D array, the higher the density of the "1" voxels in the original volume are, the lower the value will be assigned to the voxel in the inverse density volume.

In a preferred embodiment, dynamic programming based optimal spinal canal path is performed. Suppose, for example, the estimated density of a voxel is d, then 1-d is the inverse density. However, other mathematical calculations may be used to inverse the density.

FIG. 5 shows an inverse density 3D array as a cost-pointer array. From the inverse density 3D array, another 3D array named cost-pointer array is created. The cost-pointer array has the same size as the inverse density 3D array. Each element in the cost-pointer array corresponds to a voxel in the same position in the inverse density 3D array and contains two parameters: a cost value parameter and a pointer value parameter. The pointer parameter is a 3D vector which points to a physical coordinate in the original spinal canal segmentation binary image.

For the elements in the first slice 502 of the cost-pointer array, zero values are assigned to all the costs values, and each pointer value is set as the coordinate of its own corresponding voxel. Setting the index of the current slice 504 as i+1, the index of the neighboring slice below the current slice 506 is i. For any voxel $V_{i+1,j}$ in the current slice 504 of the inverse density array, calculate the cost from neighboring voxels in a defined region in slice i 506. Cost between any voxel $V_{i+1,j}$ in slice i+1 and voxel in slice $V_{i,k}$, is calculated according to equation (1).

$$\text{cost}(V_{i+1,j}, V_{i,k}) = \text{cost}(V_{i,k}) + w_1 \cdot \text{distance}(V_{i+1,j}, V_{i,k}) + w_2 \cdot \text{Inverse\_density}_{i,k} \quad (1)$$

From equation (1) any voxel $V_{i+1,j}$ in slice i+1 gets a few cost values. The minimum cost value is assigned as the cost value of any voxel $V_{i+1,j}$ in the cost-pointer array, where $V_{i,K}$ has the minimum cost to voxel $V_{i+1,j}$.

Equation (2) describes the cost for voxel $V_{i+1,j}$ and the pointer, where coordinate ($V_{i,K}$) is the physical coordinate of the voxel $V_{i,K}$.

$$\begin{cases} \text{cost}(V_{i+1,j}) = \min(\{\text{cost}(V_{i+1,j}, V_{i,k}) \mid k \in \text{index of neighbors}\}) \\ \text{pointer}(V_{i+1,j}) = \text{coordinate}(V_{i,K}), \text{ where } K = \\ \operatorname*{argmin}_k(\{\text{cost}(V_{i+1,j}, V_{i,k}) \mid k \in \text{index of neighbors}\}) \end{cases} \quad (2)$$

This step is the forward step. After calculating the whole cost-pointer array, move backward from the last slice 508 of the cost-point array to find the optimal path in the following way.

In the last slice 508 of the cost-pointer array, find the element with lowest cost value. Then, get the corresponding pointer. Suppose this pointer is $P_l$. $P_l$ is actually the physical coordinate of a voxel in the second last slice.

In the second to last slice, find the element at the position Pi, then n get the corresponding pointer as $P_{l-1}$. $P_{l-1}$ is the physical coordinate of a voxel in the third last slice.

Slice by slice, we can get a coordinates list as $\{P_l, P_{l-1}, P_{l-2}, \ldots, P_{l-(N-1)}\}$, where N is the total number of slices in this cost-pointer array. This coordinates list describes the optimal path.

While the invention has been illustrated and described in detail in the drawings and foregoing description, such illustrations and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like acquiring, determining, obtaining, outputting, providing, store or storing, calculating, simulating, receiving, warning, and stopping can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

The invention claimed is:

1. A method of generating an optimal spinal canal path, the method comprising:

receiving scan data as a three-dimensional array of a scanned spine image;

executing a three-dimensional voxel wise spinal canal segmentation from the received scan data to generate a binary three-dimensional array corresponding to the scanned spine image;

generating an inverse density three-dimensional array corresponding to the generated binary three-dimensional array having a size the same as the generated binary three-dimensional array;

down sampling the inverse density three-dimensional array to a predetermined size; performing programming based optimal spinal canal path finding to generate an optimal spinal canal path;

sampling the inverse three-dimensional array around the generated optimal spinal canal path with higher resolution and limited size;

performing dynamic programming based optimal spinal canal path finding to generate a revised optimal spinal canal path; repeating the sampling and the programming based optimal spinal canal path finding by incrementally increasing the resolution and decreasing the size;

determining whether an accuracy of the optimal spinal canal path satisfies a predetermined threshold; and generating a final optimal spinal canal path as a spinal canal center line, wherein a reformatted image is generated according to the final optimal spinal canal path as a spinal canal center line.

2. The method of generating an optimal spinal canal path according to claim 1, wherein spinal canal segmentation is performed using machine or deep learning techniques, wherein a value of 1 is assigned to each spinal canal voxel and a value of 0 is assigned to background in the generated binary three-dimensional array.

3. The method of generating an optimal spinal canal path according to claim 2, wherein generating the inverse density three-dimensional array includes assigning a float value to each voxel where the higher a density value of 1 voxels are in the binary three-dimensional array, the lower the float value assigned to a corresponding voxel in the inverse density three-dimensional array.

4. The method of generating an optimal spinal canal path according to claim 1, wherein the dynamic programming based optimal spinal canal path finding comprises:

creating a cost-pointer array that is a three-dimensional array corresponding to the inverse density three-dimensional array, wherein each element in the cost-pointer array comprises a cost component and a pointer component, wherein each cost component in the cost-pointer array corresponds to a voxel in a same position in the inverse density three-dimensional array, and wherein the pointer component is a three-dimensional vector which points to a physical coordinate in the binary three-dimensional array.

5. The method of generating an optimal spinal canal path according to claim 1, wherein a density estimation is applied to generate the inverse density three-dimensional array.

6. The method of generating an optimal spinal canal path according to claim 5, wherein the density estimation is performed via kernel density estimation techniques, and wherein the kernel is at least one of gaussian, linear, cosine, uniform, epanechnikov, exponential, and tophat.

7. An optimal path finding apparatus, comprising:

a memory configured to store computer executable instructions; and at least one processor configured to execute the computer executable instructions to cause the optimal path finding apparatus to:

receive scan data as a three-dimensional array of a scanned spine image; execute a three-dimensional voxel wise spinal canal segmentation from the received scan data to generate a binary three-dimensional array corresponding to the scanned spine image;

generate an inverse density three-dimensional array corresponding to the generated binary three-dimensional array having a size the same as the generated binary three-dimensional array;

down sample the inverse density three-dimensional array to a predetermined size;

perform programming based optimal spinal canal path finding to generate an optimal spinal canal path;

sample the inverse three-dimensional array around the generated optimal spinal canal path with higher resolution and limited size;

perform dynamic programming based optimal spinal canal path finding to generate a revised optimal spinal canal path;

repeat the sampling and the programming based optimal spinal canal path finding by incrementally increasing the resolution and decreasing the size; determine whether an accuracy of the optimal spinal canal path satisfies a predetermined threshold; and generate a final optimal spinal canal path as a spinal canal center line, wherein a reformatted image is generated according to the final optimal spinal canal path as a spinal canal center line.

8. The optimal path finding apparatus according to claim 7, wherein the spinal canal segmentation is performed using machine or deep learning techniques, wherein a value of 1 is assigned to each spinal canal voxel and a value of 0 is assigned to background in the generated binary three-dimensional array.

9. The optimal path finding apparatus according to claim 8, wherein the processor is configured to assign a float value to each voxel in the generated inverse density three-dimensional array, where the higher a density value of 1 voxels are in the binary three-dimensional array, the lower the float value assigned to a corresponding voxel in the inverse density three-dimensional array.

10. The optimal path finding apparatus according to claim 7, wherein the processor is further configured to create a cost-pointer array that is a three-dimensional array corresponding to the inverse density three-dimensional array, wherein each element in the cost-pointer array comprises a cost component and a pointer component, wherein each cost component in the cost-pointer array corresponds to a voxel in a same position in the inverse density three-dimensional array, and wherein the pointer component is a three-dimensional vector which points to a physical coordinate in the binary three-dimensional array.

11. The optimal path finding apparatus according to claim 7, wherein the processor is configured to apply a density estimation to generate the inverse density three-dimensional array.

12. The optimal path finding apparatus according to claim 11, wherein the density estimation is performed via kernel density estimation techniques, and wherein the kernel is at least one of gaussian, linear, cosine, uniform, epanechnikov, exponential, and tophat.

13. A non-transitory computer-readable medium having stored thereon instructions for causing processing circuitry to execute a process, the process comprising:

receiving scan data as a three-dimensional array of a scanned spine image; executing a three-dimensional voxel wise spinal canal segmentation from the received scan data to generate a binary three-dimensional array corresponding to the scanned spine image;

generating an inverse density three-dimensional array corresponding to the generated binary three-dimensional array having a size the same as the generated binary three-dimensional array;

down sampling the inverse density three-dimensional array to a predetermined size; performing programming based optimal spinal canal path finding to generate an optimal spinal canal path;

sampling the inverse three-dimensional array around the generated optimal spinal canal path with higher resolution and limited size;

performing dynamic programming based optimal spinal canal path finding to generate a revised optimal spinal canal path; repeating the sampling and the programming based optimal spinal canal path finding by incrementally increasing the resolution and decreasing the size;

determining whether an accuracy of the optimal spinal canal path satisfies a predetermined threshold; and generating a final optimal spinal canal path as a spinal canal center line, wherein a reformatted image is generated according to the final optimal spinal canal path as a spinal canal center line.

* * * * *